United States Patent [19]
Keeler et al.

[11] Patent Number: 5,386,373
[45] Date of Patent: Jan. 31, 1995

[54] VIRTUAL CONTINUOUS EMISSION MONITORING SYSTEM WITH SENSOR VALIDATION

[75] Inventors: James D. Keeler; John P. Havener; Devendra Godbole; Ralph B. Ferguson, all of Austin, Tex.

[73] Assignee: Pavilion Technologies, Inc., Austin, Tex.

[21] Appl. No.: 102,405

[22] Filed: Aug. 5, 1993

[51] Int. Cl.$^6$ .............................................. G05B 13/02
[52] U.S. Cl. ...................................... 364/577; 395/21; 364/500; 364/495; 364/150; 364/151; 364/222.1; 364/226.7; 364/226.8; 364/221.1; 364/221.3; 364/221.7; 364/571.04; 364/571.05
[58] Field of Search ............... 73/1 G, 1 R, 23.21, 73/31.02, 31.01, 31.03; 395/20, 21, 22, 23, 904, 906, 907; 364/500, 551.01, 150, 151, 152, 571.01–571.08, 577, 578, 579, 492, 495, 474.15, 474.16, 474.19, 222.1, 226.7, 226.8, 226.9, 221–221.9

[56] References Cited

U.S. PATENT DOCUMENTS

| | | | |
|---|---|---|---|
| 3,859,541 | 1/1975 | Hattori et al. | 307/10 R |
| 3,871,338 | 3/1975 | Schmidt et al. | 123/32 EA |
| 3,875,907 | 4/1975 | Wessel et al. | 123/32 EA |
| 3,903,853 | 9/1975 | Kizler et al. | 123/32 EA |
| 3,916,848 | 11/1975 | Schmidt | 123/32 EA |
| 3,919,983 | 11/1975 | Wahl et al. | 123/32 EA |
| 3,962,866 | 6/1976 | Neidhard et al. | 60/276 |
| 4,007,589 | 2/1977 | Neidhard et al. | 60/276 |
| 4,077,207 | 3/1978 | Hattori et al. | 60/276 |
| 4,161,883 | 7/1979 | Laird et al. | 73/863.24 |
| 4,167,161 | 9/1979 | Nakagami | 123/75 B |
| 4,171,690 | 10/1979 | Hosaka et al. | 123/119 CC |
| 4,315,243 | 2/1982 | Calvert, Sr. | 123/198 R X |
| 4,403,473 | 9/1983 | Gladden | 60/274 |
| 4,528,918 | 7/1985 | Sato et al. | 110/347 |
| 4,825,353 | 4/1989 | Jenkins | 364/152 |

(List continued on next page.)

FOREIGN PATENT DOCUMENTS 199144  8/1989  Japan ................................. 73/31.03

OTHER PUBLICATIONS

Jahnke, Ph.D., James A. *Continuous Emission Monitoring.* New York: Van Nostrand Reinhold, 1993. Book.

"Detection of Gross Errors in Nonlinearly Constrained Data: A Case Study" by R. W. Serth, C. M. Valero and W. A. Heenan, *Chm. Eng. Comm.* 1987, vol. 51, pp. 89–104.

"Diagnosis Using Backpropagation Neural Network—Analysis and Criticism" by M. A. Kramer and J. A. Leonard, *Computers Chem. Engng.*, vol. 14, No. 14, pp. 1323–1338, 1990.

"Autoassociative Neural Networks" by M. A. Kramer, *Computers Chem Engng.*, vol. 16, No. 4, pp. 313–328, 1992.

"Gross Error Detection and Data Reconciliation in Steam-Metering Systems" by R. W. Serth and W. A. Heenan, *AIChE Journal,* May 1986, vol. 32, No. 5, pp. 733–742.

*Primary Examiner*—Thomas P. Noland
*Attorney, Agent, or Firm*—Gregory M. Howison

[57] ABSTRACT

A continuous emission monitoring system for a manufacturing plant (10) includes a control system (16) which has associated therewith a virtual sensor network (18). The network (18) is a predictive network that receives as inputs both control values to the plant (10) and also sensor values. The network (18) is then operable to map the inputs through a stored representation of the plant (10) to output a predicted pollutant sensor level. This predicted pollutant sensor level is essentially the prediction of an actual pollutant sensor level that can be measured by a pollutant sensor (14). The network (18) therefore is a substitute for the pollutant sensor (14), thus providing a virtual sensor. The sensor values from the plant (10) are first processed through a sensor validation system (22). The sensor validation system (22) is operable to determine which of the sensors falls outside of acceptable limits and then substitutes therefor a predicted output, such that the inputs to the virtual sensor network (18) are within acceptable limits.

86 Claims, 5 Drawing Sheets

U.S. PATENT DOCUMENTS

| | | | |
|---|---|---|---|
| 5,003,950 | 4/1991 | Kato et al. | 123/422 |
| 5,025,499 | 6/1991 | Inoue et al. | 395/900 X |
| 5,077,970 | 1/1992 | Hamburg | 60/274 |
| 5,088,314 | 2/1992 | Takashi | 73/31.03 X |
| 5,093,792 | 3/1992 | Taki et al. | 364/431.01 |
| 5,113,483 | 5/1992 | Keeler et al. | 395/23 |
| 5,119,287 | 6/1992 | Nakamura et al. | 364/148 |
| 5,119,468 | 6/1992 | Owens | 364/151 X |
| 5,150,682 | 9/1992 | Magnet | 123/417 |
| 5,163,412 | 11/1992 | Neu et al. | 123/700 |
| 5,175,678 | 12/1992 | Frerichs et al. | 364/165 X |
| 5,177,464 | 1/1993 | Hamburg | 340/439 |
| 5,213,080 | 5/1993 | Lambert et al. | 123/417 |
| 5,220,905 | 6/1993 | Lundahl | 123/681 |
| 5,222,471 | 6/1993 | Stueven | 123/695 |
| 5,228,335 | 7/1993 | Clemmens et al. | 73/118.1 |
| 5,231,939 | 8/1993 | Tanaka | 110/347 |
| 5,251,285 | 10/1993 | Inoue et al. | 364/160 X |
| 5,270,009 | 12/1993 | Nakamori et al. | 73/31.01 X |
| 5,271,674 | 12/1993 | Kalmanovitch | 374/16 |

VIRTUAL CONTINUOUS EMISSION MONITORING SYSTEM WITH SENSOR VALIDATION

TECHNICAL FIELD OF THE INVENTION

The present invention pertains in general to emission monitoring systems, and more particularly, to a system that replaces the continuous emission monitor with a virtual sensor implemented with a neural network, which neural network incorporates a sensor validation network to identify and replace faulty sensors for input to the network.

BACKGROUND OF THE INVENTION

As public awareness increases with respect to the environment, industry is required to make significant changes. Although industry is somewhat responsive to public opinion, government regulatory bodies are typically brought in to ensure that public needs are met. In order to do this, government sets up regulatory arms of already existing branches of entities such as the Environmental Protection Agency. These arms are given the task of putting in place policies regarding toxic waste, emissions, etc., that may effect the environment. Further, these regulatory bodies are also given the task of enforcing these regulations. One particular area that has received a great deal of attention in recent years is that of monitoring emissions of noxious gases being placed into the atmosphere by manufacturing facilities.

Typically, the technique for ensuring that noxious gases are being correctly monitored has been to implement Continuous Emissions Monitoring systems (CEM). These systems are utilized to monitor the amount of emissions such as Sulfur Dioxide ($SO_2$), Nitrogen Oxides (NOx), Carbon Monoxide (CO), Total reduced Sulfur (TRS), opacity, Volatile Organic Carbon (VOC), and hazardous substances of all sorts. The classical way of monitoring of these emissions is to install a Continuous Emission Monitor (CEM) in the plant on each emission point source. Regulatory Agencies provide for each plant guidelines as to how the output is to be regulated, i.e., define the acceptable limit of the emissions.

The classic CEM is composed of either an in situ analyzer installed directly in the stack, or an extractive system which extracts a gas sample and conveys it to an analyzer at grade level. However, these sensors are quite expensive, difficult to maintain, and difficult to keep properly calibrated. As such, the regulations that deal with a CEM system require the sensors to be calibrated frequently, which calibration procedure can take a number of hours, due to the complexity thereof. Regulations allow a maximum downtime of ten percent for calibration. If a unit remains in operation greater than ten percent of the time with the CEM down, the emissions level is considered by the Regulators to be at maximal potential level. This results in out-of-compliance operation. Most manufactures will shut down operation rather than face the high penalties of such occurrence. One of the reasons for this is that the operation of the plant relative to the monitoring of the NOx emissions must be "truly continuous" such that no leeway is provided for faulty sensors, sensors that have fallen out of calibration, etc. One solution to this has been to utilize redundant sensors, which is a very expensive solution. Therefore, there exists a need to provide a system that does not require the presence of a sensor while still ensuring that the output of the plant is within tolerances relative to noxious emissions.

SUMMARY OF THE INVENTION

The present invention disclosed and claimed herein comprises a method and apparatus for monitoring emissions in a manufacturing plant that is operable to generate as a by-product pollutants. The manufacturing plant has associated therewith controls to alter the operation of the plant and sensors to measure the operating parameters of the plant. The level of pollutants emitted by the plant is measured to determine the level thereof. The control values to the plant are provided and the sensor values of the plant are provided. A stored representation of the plant is provided in association with a virtual sensor predictive network providing as an output a predicted pollutant level that is a prediction of the actual pollutant level output by the manufacturing plant. The control values to the plant and the sensor values from the plant comprise the inputs to the virtual sensor predictive network. The stored representation in the virtual sensor predictive network is learned from measured pollutant levels, the control values and the sensor values. The plant utilizes the predicted pollutant level to provide control thereof in accordance with a predetermined control scheme.

In another aspect of the present invention, the virtual sensor predictive network is a non-linear network that is trained on a set of training data. The set of training data is generated by the step of measuring the level of pollutants, the control values and the sensor values. Periodically, the pollutant levels are measured to generate data therefor on a time base. This information is merged with the information provided by the control values to the plant and the sensor values from the plant. This provides the training database. The predictive network is trained on this information to provide the stored representation. The inputs to the network, the control values and the sensor values, are then mapped through the stored representation to provide the predicted pollutant level.

In a further aspect of the present invention, the sensor values are monitored to determine if they fall outside of acceptable limits in accordance with predetermined criteria. If they do fall outside of acceptable limits, a known value is substituted therefor as an input to the virtual sensor predictive network. The known value is a predicted value, which is determined as a function of the other sensor values.

In a yet further aspect of the present invention, the sensor values are determined to be outside of acceptable limits by processing the sensor values through a sensor validation predictive network that maps the sensor values through a stored representation of the sensor values, wherein a predicted sensor value is provided for each of the actual sensor values and the stored representation is a function of each of the actual sensor values provided as an input to the sensor validation predictive network. When a predicted sensor value is determined to be outside of acceptable limits, the predicted sensor value is then substituted on the input to the sensor validation predictive network as an input in place of the corresponding actual sensor value and the predicted sensor value utilized to provide the substituted known value.

BRIEF DESCRIPTION OF THE DRAWINGS

For a more complete understanding of the present invention and the advantages thereof, reference is now made to the following description taken in conjunction with the accompanying Drawings in which:

FIG. 5b illustrates a detail of the iterate operation of FIG. 5a;

FIG. 6 illustrates a detail of a typical plant, a boiler for a steam generation facility;

DETAILED DESCRIPTION OF THE INVENTION

Figure 1:
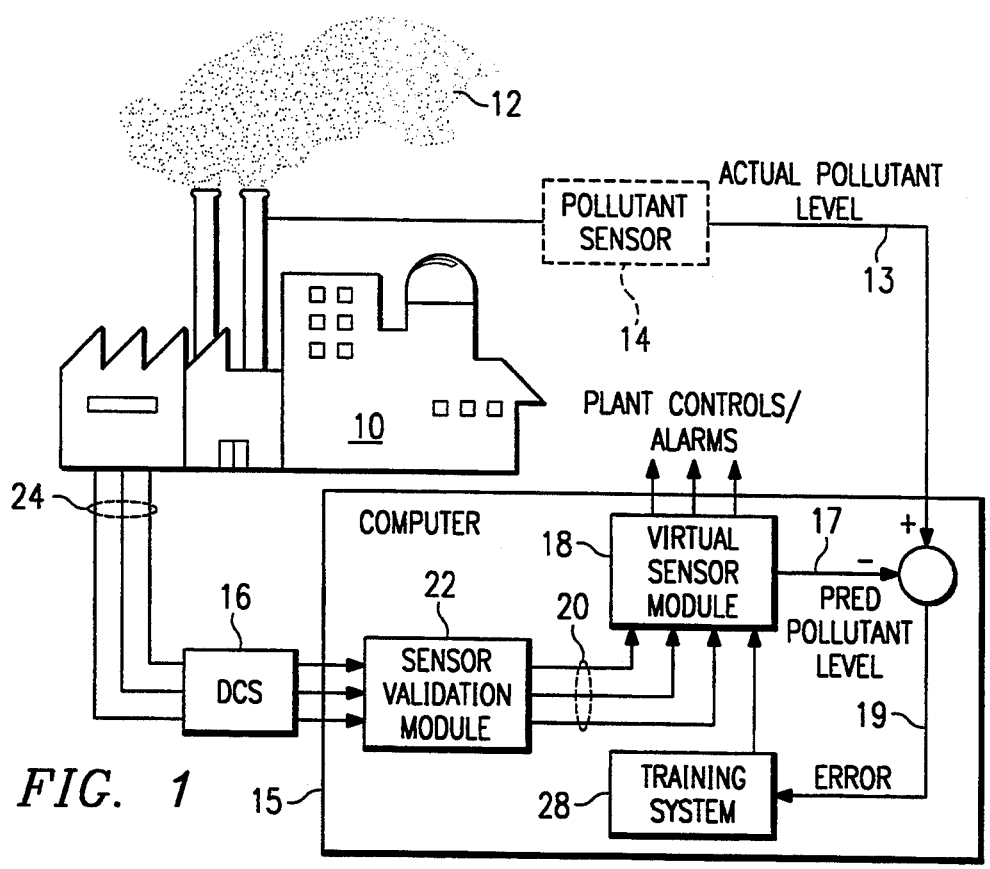
FIG. 1 illustrates an overall block diagram of the virtual sensor of the present invention.

Referring now to FIG. 1, there is illustrated an overall block diagram of the system of the present invention. A plant 10 is provided that, during the normal operation thereof, releases some emissions 12 containing some level of pollutants. The pollutants 12 are monitored by a pollutant sensor 14 or by utilization of EPA established reference methods, which sensor 14 is illustrated in phantom, to provide continuous emission monitoring. This is referred to as a CEM. As will be described hereinbelow, the present invention provides a virtual sensor operation wherein the pollutant sensor 14 is only required for initial training of virtual sensor network. The pollutant sensor 14 is utilized to gather training data to be combined with the control values and sensor values that are available to a Distributed Control System (DCS) 16, generally referred to as the plant information system. The DCS 16 provides control values associated with control inputs to the system and sensor values to a computer 15. The computer 15 is comprised of a virtual sensor network 18 that essentially provides a non-linear representation of the plant 10, which non-linear representation is a "learned" representation. The virtual sensor network 18 is operable to receive run time inputs 20 from a sensor validation system 22. The sensor validation system 22 is operable to receive actual measured inputs 24 from the plant 10 through the DCS 16. These measured inputs represent measured state variables of the plant in the form of sensor values and also control values that are input to the plant to provide control therefor. As will be described hereinbelow, the various inputs 24 are provided as inputs to the virtual sensor network 18 through the DCS 16. However, some of these inputs may be faulty and the sensor validation system 22 is operable to generate an alarm when any of the attached sensors fails and to replace failed sensor values with reconciled sensor values.

The virtual sensor network 18 is operable to receive the inputs 20 and predict plant controls and alarms. The virtual sensor network 18 can predict what the pollutant levels are that normally would be monitored by the pollutant sensor 14; hence, it provides a virtual sensor. The sensor network 18 is a network that can be trained with a training system 28. The training system 28 utilizes as a target the actual pollutant level on a line 13 as measured by the pollutant sensor 14 when it is present, and also the inputs 24 from the plant 10. The difference between the predicted pollutant level on a line 17 and the actual pollutant level on line 13 generates an error on line 19 that is used by the training system to adjust the stored representation in the virtual sensor module, so as to minimize the error. In operation, as will be described in more detail hereinbelow, the pollutant sensor 14 is a Continuous Emissions Monitor (CEM) that is operable to be temporarily connected to the plant 10 to monitor the level of the pollutants 12. This provides a target to the training system 28. The network 18 is then trained with both the measured plant sensor and control values, not including the CEM output, and the CEM output when present. This information is utilized to generate a training dataset.

After training, the pollutant sensor 14 is removed and then the system operates by predicting what the output of the CEM or pollutant sensor 14 would be. The virtual sensor network 18 then replaces the pollutant sensor 14 and then can be utilized in a control function to predict plant control/alarms to maintain the operation of the plant 10 within acceptable standards. Further, the virtual sensor network 18 can be used solely to provide an output in place of the pollutant sensor 14 that can be utilized by the operator of the sensor to ensure that all necessary procedures are being followed to ensure that the level of pollutants is within acceptable ranges. For example, if the predicted output from the network 18 exceeded one of the established guidelines or thresholds, the operator would then follow certain prescribed procedures to correct the situation. This would be the case even if the pollutant sensor 14 were present. The advantage to this is that the relatively expensive and difficult to maintain pollutant sensor 14 would not have to be present. Further, a new pollutant sensor 14 or a portable pollutant sensor 14 is periodically utilized to check the operation of a virtual sensor network 18 to ensure that it is operating correctly and that no parameters of the plant have changed such that the prediction is now incorrect or the model no longer represents the plant. In this manner, the system would have to be retrained by using a new set of training data that would be provided by the operation of the connecting the pollutant sensor 14 to the plant 10. This could be the situation wherein some measurement device degraded or the plant itself had physically changed parameters due to capital improvements, age, etc.

In another mode of operation, the pollutant sensor 14 may be in a situation where it might be removed from the plant 10 for calibration purposes. During this time, the virtual sensor network 18 is then utilized to replace the sensor 14 during the calibration procedure.

Figure 1A:
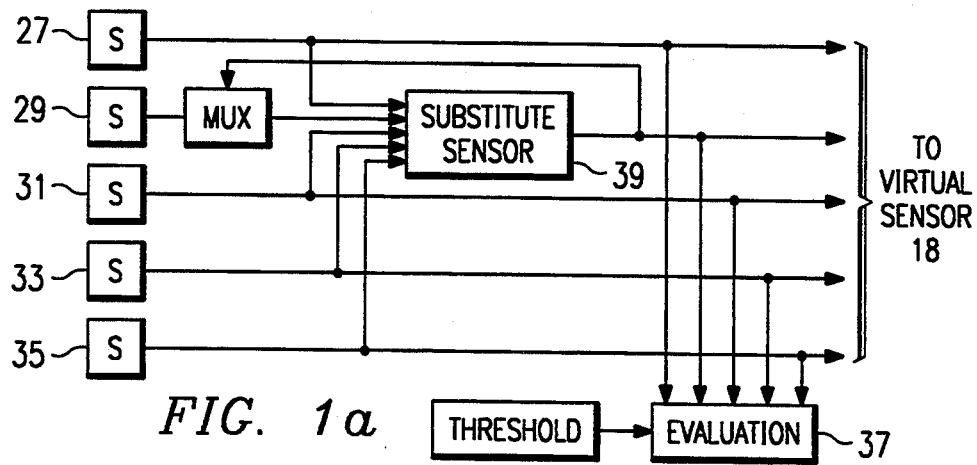
FIG. 1a illustrates a diagrammatic view of the sensor validation system.

Referring now to FIG. 1a, there is illustrated a block diagram of the operation of the sensor validation system 22. A plurality of sensors 27, 29, 31, 33 and 35 are illustrated. Each of the sensors 27, 29, 31, 33 and 35 have an output that is connected to the input of the virtual sensor 18. Additionally, each of the outputs is connected to an evaluation system 37 to determine if the sensor is valid, as will be described hereinbelow. When any one of the sensors 27, 29, 31, 33 and 35 is determined to be faulty, it is replaced by a substitute sensor 39, which is a predicted sensor value that predicts the output of the faulty sensor utilizing a stored representation of the faulty sensor, which stored representation is a function of the other sensors 27, 29, 31, 33 and 35. Therefore, the substitute sensor 39 requires as inputs the outputs of the valid sensors and the predicted output of the substitute sensor. This is illustrated in FIG. 1a with the sensor 29 being substituted, with the substitute sensor 39 receiving as inputs the outputs of the sensors 27, 31, 33 and 35 and, in place of the output of the sensor 29, the predicted output of the substitute sensor 39. Further, another sensor could be substituted for with the output of the substitute sensor 39 being an input for the new and additional sensor (not shown).

Figure 2:
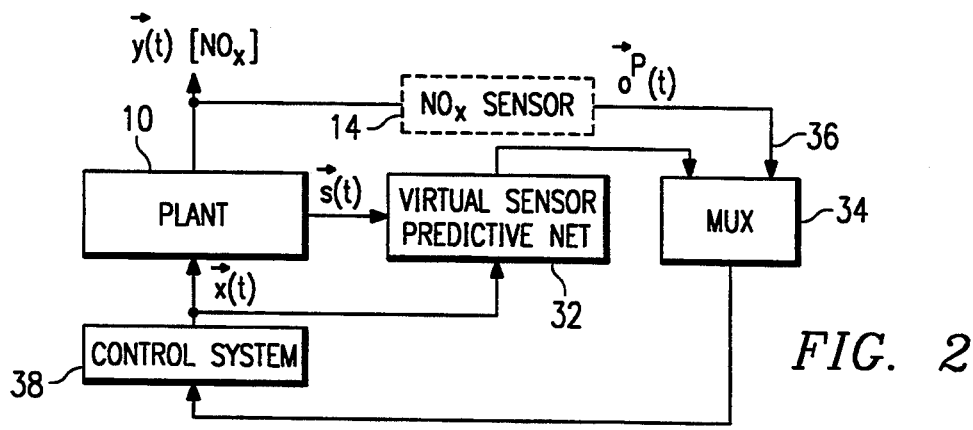
FIG. 2 illustrates a block diagram of the relation of the virtual sensor and the control system.

Referring now to FIG. 2, there is illustrated a block diagram for the operation wherein a virtual sensor predictive network 32 is provided which is operable to receive measured plant sensor values s(t) from the plant 10 and also the control values x(t) which are inputs to the plant 10. The virtual sensor predictive network 32 is operable to output a predicted virtual sensor value $o^p(t)$ for input to a multiplexer 34. The sensor value from sensor 14 is input on the line 36 to the multiplexer 34. The multiplexer 34 is operable to select either the predicted output of the network 32 or the actual output of the sensor 14 for input to a control system 38. The control system 38 is operable to generate the input values x(t) to the plant 10. The multiplexer 34 represents the operation wherein the output of the network 32 is utilized to replace that of the sensor 14.

Figure 3:
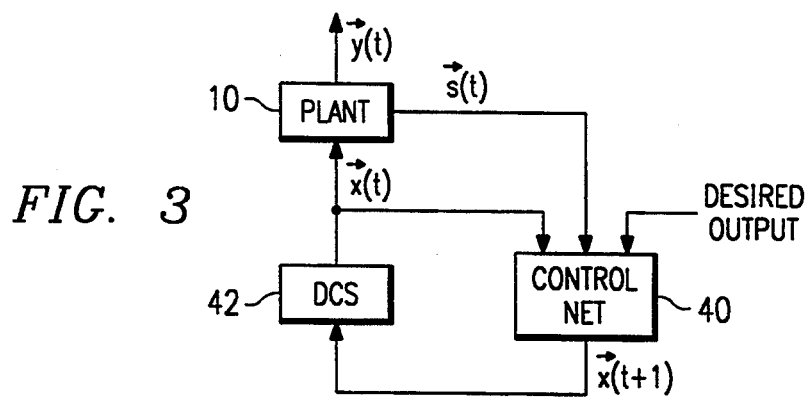
FIG. 3 illustrates an embodiment utilizing a single control network.

Referring now to FIG. 3, there is illustrated one embodiment of the system of the present invention wherein a dynamic control system is provided. In this system, a control network 40 is provided which receives as an input the control input values x(t) and the sensor values s(t), the sensor values s(t) comprise the measured plant variables such as flow meter measurements, temperature measurements, etc. In addition, the control net 40 is operable to receive a desired output value as one of the inputs. The control net 40 contains a stored representation of the plant and is operable to output a set of control input values x(t+1). These are input to a Distributed Control System (DCS) 42, which is operable to generate the control values x(t). The control network 40 is a conventional control network that is trained on a given desired input, and which control network 40 is operable to receive the sensor values and control values and generate the updated control values x(t+1) that are necessary to provide the desired outputs. The control network 40 is generally comprised of a neural network having associated therewith weights that define the representation that is stored in the neural network. In the embodiment of FIG. 3, these weights are frozen and were learned by training the control network 40 on a given desired output with a given set of training data for the control values x(t) and the sensor values s(t). A desired output is provided as one input for selecting between sets of weights. The general operation of control nets is described in W. T. Miller, III, R. S. Sutton and P. J. Werbos, "Neural Networks for Control", *The MIT Press*, 1990, which reference is incorporated herein by reference.

Figure 4:
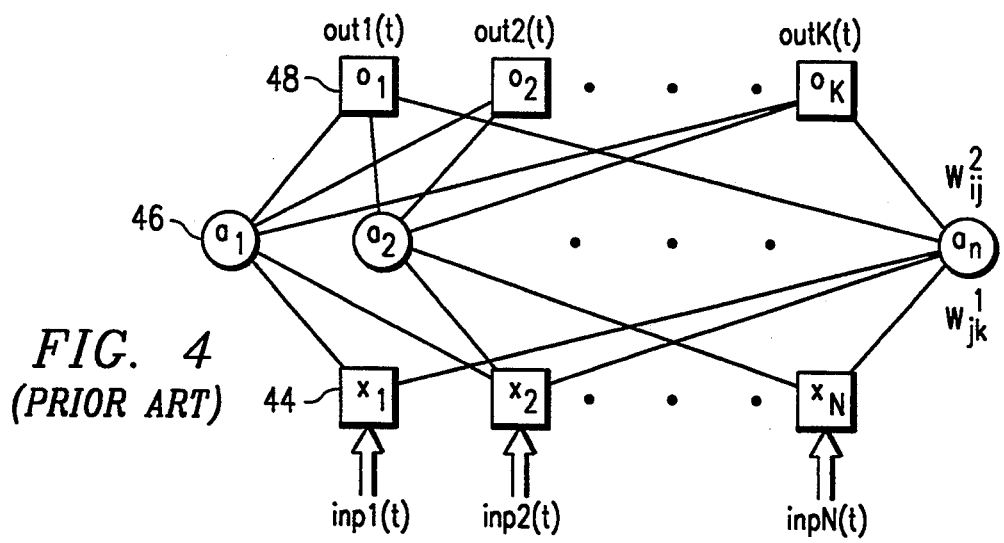
FIG. 4 illustrates a diagrammatic view of a conventional neural network.

Referring now to FIG. 4, there is illustrated a detailed diagram of a conventional neural network comprised of input nodes 44, hidden nodes 46 and output nodes 48. The input nodes 44 are comprised of N nodes labelled $x_1, x_2, \ldots x_N$, which are operable to receive an input vector x(t) comprised of a plurality of inputs, INP1(t), INP2(t), ... INPN(t). Similarly, the output nodes 48 are labelled $o_1, o_2, \ldots o_K$, which are operable to generate an output vector o(t), which is comprised of the output OUT1(t), OUT2(t), ... OUTK(t). The input nodes 44 are interconnected with the hidden nodes 46, hidden nodes 46 being labelled $a_1, a_2, \ldots a_n$, through an interconnection network where each input node 44 is interconnected with each of the hidden nodes 46. However, some interconnection schemes do not require full interconnection. Each of the interconnects has a weight $W_{ij}^1$. Each of the hidden nodes 46 has an output $o_i$ with a function g, the output of each of the hidden nodes defined as follows:

$$\vec{a} = g\left(\sum_{i=1}^{N} W_{ij}^1 x_i + b_j^1\right) \quad (1)$$

Similarly, the output of each of the hidden nodes 46 is interconnected with substantially all of the output nodes 48 through an interconnect network, each of the interconnects having a weight $W_{jk}^2$ associated therewith. The output of each of the output nodes is defined as follows:

$$\vec{O}_k = g\left(\sum_{j=1}^{n} W_{jk}^2 a_j + b_k^2\right) \quad (2)$$

This neural network is then trained to learn an function f(x(t), P) as follows:

$$\vec{o}(t) = \vec{f}(\vec{x}(t), \vec{P}) \quad (3)$$

where o(t) is an output vector and P is a vector or parameters ("weights") that are variable during the learning stage. The goal is to minimize the Total-Sum-Square-Error function:

$$\vec{E} = \sum_{t=1}^{N} (\vec{y}(t) - \vec{o}(t))^2 \quad (4)$$

The Total-Sum-Square-Error function is minimized by changing the parameters P of the function f. This is done by the back propagation or a gradient descent method in the preferred embodiment on the parameters $W_{jk}^2$, $W_{ij}^1$, $b_{j}^1$, $b_{k}^2$. This is described in numerous articles, and is well known. Therefore, the neural network is essentially a parameter fitting scheme that can be viewed as a class of statistical algorithms for fitting probability distributions. Alternatively, the neural network can be viewed as a functional approximator that fits the input-output data with a high-dimensional surface. The neural network utilizes a very simple, almost trivial function (typically sigmoids), in a multi-layer nested structure.

The neural network described above is just one example. Other types of neural networks that may be utilized are those using multiple hidden layers, radial basis functions, gaussian bars (as described in U.S. Pat. No. 5,113,483, issued May 12, 1992, which is incorporated herein by reference), and any other type of general neural network. In the preferred embodiment, the neural network utilized is of the type referred to as a multi-layer perceptron.

Figure 5A:
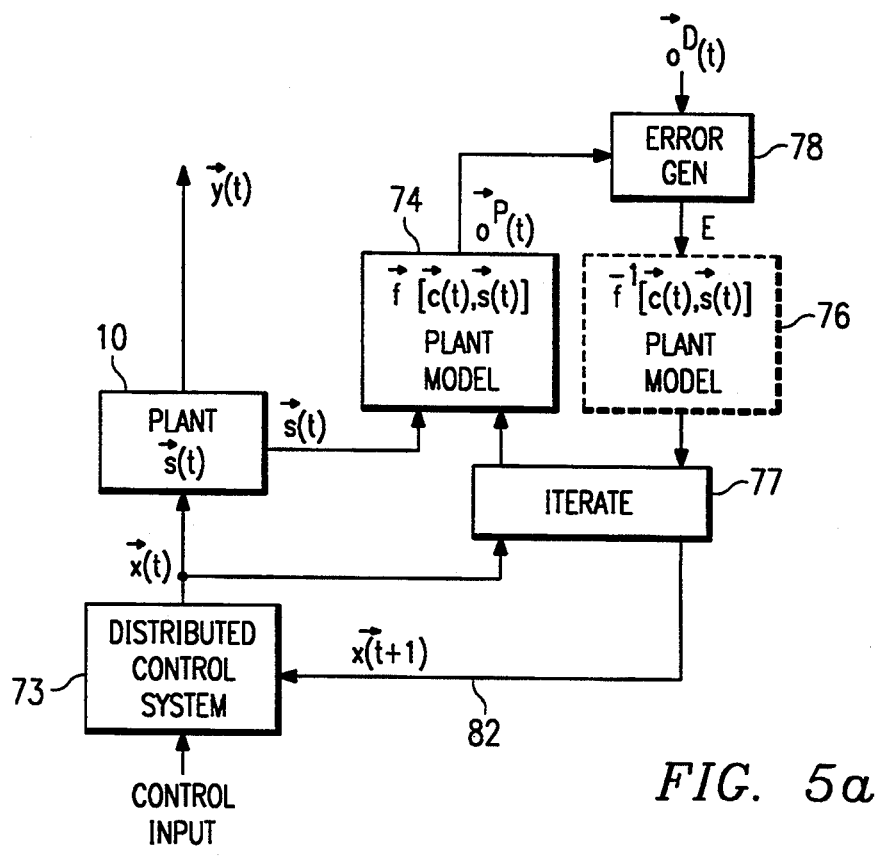
FIG. 5a illustrates a more detailed block diagram of the control network.

Referring now to FIG. 5a, there is illustrated a block diagram of a control system for optimization/control of a plant's operation. The plant 10 has an input for receiving the control values x(t) and an output for providing the actual output y(t) with the sensor values s(t) being associated therewith, these being the internal state variables. A plant predictive model 74 is developed with a neural network to accurately model the plant in accordance with the function f(x(t),s(t)) to provide an output $o^p(t)$, which represents the predicted output of plant predictive model 74. The inputs to the plant model 74 are the control values x(t) and the sensor values s(t). For purposes of optimization/control, the plant model 74 is deemed to be a relatively accurate model of the operation of the plant 72. In an optimization/control procedure, an operator independently generates a desired output value $o^d(t)$ for input to an error generation block 78 that also receives the predicted output $o^p(t)$. An error is generated between the desired and the predicted outputs and input to an inverse plant model 76 which is identical to the neural network representing the plant predictive model 74, with the exception that it is operated by back propagating the error through the original plant model with the weights of the predictive model frozen. This back propagation of the error through the network is similar to an inversion of the network with the output of the plant model 76 representing a $\Delta x(t+1)$ utilized in a gradient descent operation illustrated by an iterate block 77. In operation, the value $\Delta x(t+1)$ is added initially to the input value x(t) and this sum then processed through plant predictive model 74 to provide a new predicted output $o^p(t)$ and a new error. This iteration continues until the error is reduced below a predetermined value. The final value is then output as the new predicted control values x(t+1).

This new x(t+1) value comprises the control values that are required to achieve the desired actual output from the plant 72. This is input to a control system 73, wherein a new value is presented to the system for input as the control values x(t). The control system 73 is operable to receive a generalized control input which can be varied by the distributed control system 73. The general terminology for the back propagation of error for control purposes is "Back Propagation-to-Activation" (BPA).

In the preferred embodiment, the method utilized to back propagate the error through the plant model 76 is to utilize a local gradient descent through the network from the output to the input with the weights frozen. The first step is to apply the present inputs for both the control values x(t) and the sensor values s(t) into the plant model 74 to generate the predicted output $o^p(t)$. A local gradient descent is then performed on the neural network from the output to the input with the weights frozen by inputting the error between the desired output $o^d(t)$ and the predicted output $o^p(t)$ in accordance with the following equation:

$$\Delta \bar{x}(t) = \bar{x}(t+1) - \bar{x}(t) = \eta \frac{\partial (\bar{o}^d(t) - \bar{o}^p(t))^2}{\partial \bar{x}(t)} \quad (5)$$

where $\eta$ is an adjustable "step size" parameter. The output is then regenerated from the new x(t), and the gradient descent procedure is iterated.

Figures 5B, 6:
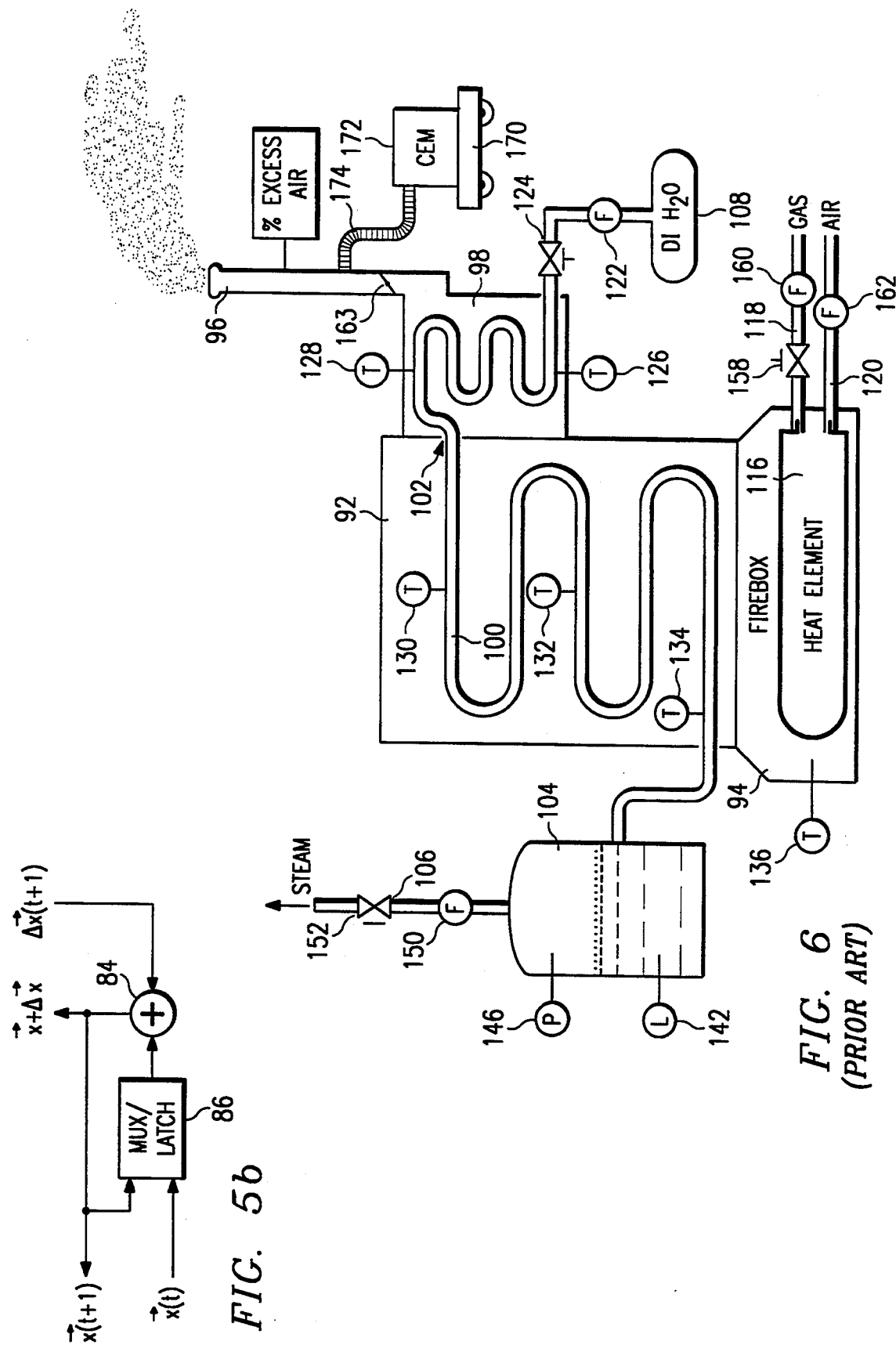

Referring now to FIG. 5b, there is illustrated a detailed block diagram of the iterate block 77. The iterate block 77 is comprised of a summing junction which is operable to receive the $\Delta x(t+1)$ input and the output of a multiplexor/latch block 86. The multiplexor/latch block 86 is operable to receive both the output of the summing junction 84 for feedback as one of the inputs and the control variable x(t). The output of the summing block 84 is the sum of the previous value of x(t) plus the new iterative change value $\Delta x(t)$. This will then be iteratively summed with the previous value to generate a new iterative value until the error is at a predetermined level. At this point, the output of the summing junction 84 will comprise the new control value x(t+1).

Another standard method of optimization involves a random search through the various control values to minimize the square of the difference between the predicted outputs and the desired outputs. This is often referred to as a monte-carlo search. This search works by making random changes to the control values and feeding these modified control values into the model to get the predicted output. The predicted output is then compared to the desired output and the best set of control values is tracked over the entire random search. Given enough random trials, a set of control values will be obtained that produces a predicted output that closely matches the desired output. For reference on this technique and associated, more sophisticated random optimization techniques, see the paper by S. Kirkpatrick, C. D. Gelatt, M. P. Vecchi, "Optimization by Simulated Annealing". *Science*, vol. 220, 671-780 (1983), which reference is incorporated herein by reference.

Referring now to FIG. 6, there is illustrated a diagrammatic view of a typical plant that may exist at a manufacturing facility. The plant typically comprises a boiler 92 which has a firebox 94 disposed at the lower end thereof. The boiler 92 interfaces with a stack 96 through a preheat chamber 98. Many tubes of which tube 100 is typical thereof are operable to run through the chamber 98 and enter the boiler 92. The tube 100 then passes in a serpentine manner through the boiler 92 to an output pressure vessel 104, which is pressurized. The vessel 104 is operable to generate steam out of an outlet 106. The other end of the tube 100 that enters the chamber 98 is connected to a source 108 of the deionized water. In operation, the water is passed through the tube 100 to the chamber 98, which picks up heat therein and then into the main boiler 92, where it is heated further. This then passes through to the vessel 104. The firebox 94 has a heating element 116 associated therewith that is operable to receive gas through a gas line 118 and air through an air line 120. The mixture of the gas and the air allows the heating element 116 to generate heat in the firebox 94 and heat up the water in the tube 100 within the boiler 92.

The tube 100, when it exits the source 108 with the deionized water at the source, has the flow thereof measured by the flow meter 122. A valve 124 allows control of the flow of fluid from the source 108 into the chamber 98. Two temperature sensors 126 and 128 are provided at different locations along the tube 100 within the chamber 90 to provide temperature measurements therefor. Additionally, temperature sensors 130, 132 and 134 are provided along the tube 100 at various locations within the main boiler 92. A temperature sensor 136 is provided for the firebox 94. The level of the fluid within the pressure vessel 104 is measured by a level meter 142 and the pressure therein is measured by a pressure meter 146. A flow meter 150 is provided for measuring the flow of steam out of the pressure vessel and a control valve 152 provides control of the steam exiting the pressure vessel 104. The heater element 116 is controlled with a valve 158 on the gas line, which has the flow thereof measured by a flow meter 160. The flow meter on the air line 120 is measured by a flow meter 162. A damper 163 in the stack 96 is utilized to control air flow through the firebox 94.

It can be seen that the sensor values s(t) of the plant are provided by the various temperature and flow measurement devices. Further, the control values, in the form of the various valves and damper positions provide the control values to the plant. Therefore, an operator can control the operation of the plant by controlling the various flow meters and other control values, some of which are not illustrated. The remaining inputs that are necessary in order to provide adequate control of the plant for the purpose of continuous emission monitoring are the NOx levels. These are provided by the virtual sensor network 18 of FIG. 1. However, as described above, periodically a portable unit 170, having disposed thereon a CEM 172, is connected via a duct 174 to the stack 96 to measure the amount of NOx in the output emissions to the air. The CEM 172 then generates a report as to the level of the NOx. If this level is within acceptable standards, then this is merely reported. However, if the level is outside of acceptable limits, this is reported to the plant operator and either changes are made or the plant is shut down. Additionally, the information generated by the CEM 172 is generated on a time base and this comprises training data. This training data, since it is on a common time base, can then be combined or merged with data associated with the sensor values and the control values, which are also on a time base, to provide new training data for the virtual sensor network 18. This can be utilized by the training system 20 to retrain the virtual sensor network 18, if necessary.

Figure 7:
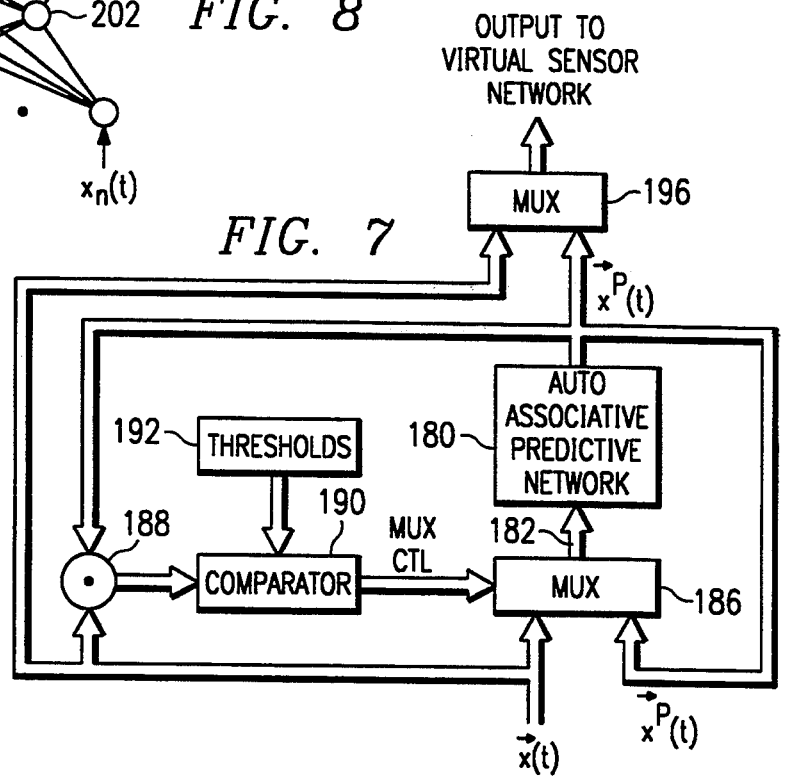
FIG. 7 illustrates a block diagram of the sensor validation network.

Referring now to FIG. 7, there is illustrated a block diagram of the preferred embodiment for the sensor validation system 22. To ensure that the overall inputs x(t) to the network 18 are "valid", it is necessary to perform some type of comparison with expected or predicted values. If it is suspected that the generated values are not accurate, then an alarm is generated to advise the plant operator or the control system of the need to calibrate the sensor or to repair the sensor, and an estimated or predicted value for that sensor value is substituted for the actual measured value of the sensor.

In a preferred embodiment, an auto associative predictive neural network 180 is provided which is a network having an input layer for receiving select ones of the inputs x(t) on an input 182. Although not illustrated, only certain ones of the actual sensor values are necessary as inputs to the virtual sensor network 18 in order to provide an accurate prediction of the NOx levels that would generally be provided by the pollutant sensor 14. These are determined by performing a sensitivity analysis. This is described in U.S. patent application Ser. No. 056,197, filed Apr. 30, 1993 and entitled "Method and Apparatus for Determining the Sensitivity of Inputs to a Neural Network on Output Parameters" (Atty. Dkt. No. PAVI-21,761), which is assigned to the present Assignee. By utilizing the sensitivity analysis, the number of inputs to the network 18 can be significantly reduced and only the important inputs utilized. This significantly reduces the size of the auto associative predictive network 180 and also the virtual sensor network 18.

The actual inputs x(t) are input to a multiplexer 186 which is operable to select between the predicted inputs $x^p(t)$ output by the network 180, which is a predicted output, and the actual inputs x(t). In operation, a first cycle occurs when the multiplexer selects the actual inputs x(t). The predicted inputs $x^p(t)$ are then input to a subtraction circuit 188 to determine the difference between x(t) and $x^p(t)$. This difference is input to comparator 190 for comparison with thresholds stored in a threshold memory 192. The one of the actual inputs to the network 180 having associated therewith the largest error as compared to the acceptable threshold is then connected to the associated predicted output of the network 180. The actual inputs x(t) with the substituted or reconnected input is then again cycled through the auto associative predictive network 180. On this next cycle, the difference between the actual and the predicted values are again determined, compared with the thresholds, and the one of the actual inputs having the largest error is reconnected to the associated predicted input by the multiplexer 186. This continues until all of the predicted inputs, with the determined faulty or unacceptable actual values replaced with the predicted values output by the network 180, are within a predetermined range. Once this has occurred, the predicted values from the network 180 are input to a multiplexer 196, and the multiplexer 196 selecting for output therefrom the actual values that were determined to be acceptable and the predicted values as a substitute for the actual values that were determined to be unacceptable. It should be noted that the predicted values are generated by running the network with the determined unacceptable actual values replaced with the associated predicted values by the multiplexor 186. The output of the multiplexor 196 is then input to the virtual sensor network 18.

In another embodiment of the invention, The predicted input values output by the auto associative predictive network 180 can be provided as the input to the virtual sensor network 18. This would then not require the multiplexer 196 and, in fact, the auto associative predictive network 180 can continually monitor and replace ones of the sensor inputs that are determined to be invalid.

Figure 8:
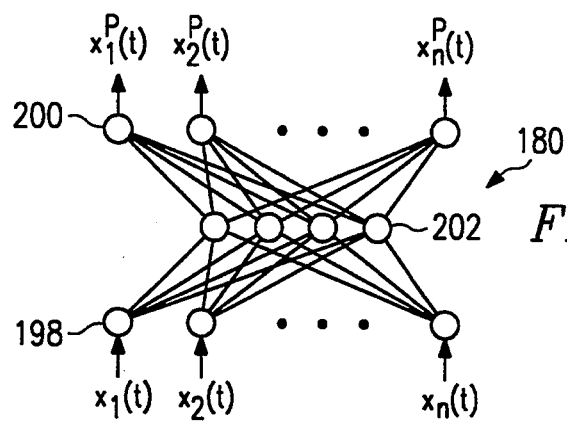
FIG. 8 illustrates a diagrammatic view of the auto associative predictive network utilized in the system of FIG. 7.

Referring now to FIG. 8, there is illustrated a diagrammatic view of the auto associative predictive network 180. The network is comprised of an input layer of nodes 198 and an output layer of nodes 200. There is one node in the layer 198 for each of the input vectors x(t), illustrated as $x_1(t)$, $x_2(t)$ ... $x_n(t)$. Similarly, there is a single node for each of the predicted output variables $x^p(t)$ such that there are outputs $x_1^p(t)$, $x_2^p(t)$ ... $x_n^p(t)$. The input layer of nodes 198 is mapped through to the output layer of nodes 200 through a hidden layer of nodes 202. The hidden layer of nodes 202 has a plurality of interconnections with each of the nodes in the input layer of nodes and each of the output layer of nodes 200.

Each of these interconnections is weighted. Further, the number of nodes in the hidden layer of nodes 202 is less than the number of nodes in either the input layer 198 or the output layer 200. This is therefore referred to as a bowtie network. The network 180 can be trained via a back propagation training technique. This is described in D. E. Rumelhart, G. E. Hinton and R. J. Williams, "Learning Internal Representations by Propagations" in D. E. Rumelhart and J. L. McClelland, *Parallel Distributive Processing*, Vol. 1, 1986.

Figure 9A:
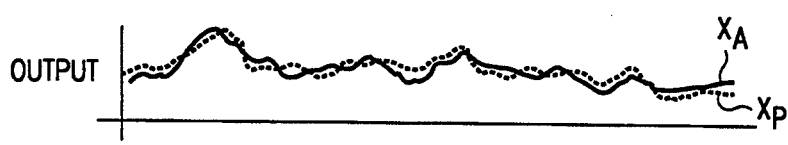
FIGS. 9a and 9b illustrate plots of predicted versus actual pollutant sensor values and the difference therebetween.
Figure 9B:

Referring now to FIGS. 9a and 9b, there are illustrated two plots depicting operation of the sensor validation system 22. The actual inputs are represented by $X_A$ and the predicted input is represented by $X_p$. It can be seen that the predicted input does not exactly follow the actual input, it being noted that the actual input is actually the input to the overall system. The difference between the actual and the predicted input values is illustrated in FIG. 9b.

Figure 10A:
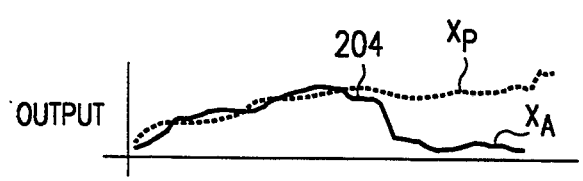
FIGS. 10a and 10b illustrate the plots of FIGS. 9a and 9b, respectively, wherein one of the sensors is faulty.
Figure 10B:
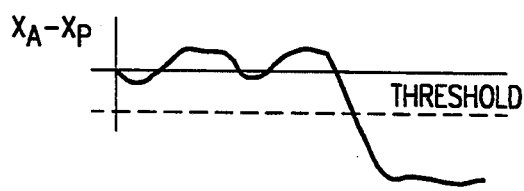

Referring now to FIGS. 10a and 10b, there is illustrated corresponding plots to those of FIGS. 9a and 9b with the exception that the sensor generating the actual input fails. It can be seen that up to a point 204 on the curve $X_a$, the predicted and actual sensor values track fairly well with minimal error. However, at the point 204 the error increases dramatically, indicating that the sensor no longer provides an value that corresponds to the predicted value. This is illustrated in FIG. 10b, wherein the error increases. When the difference between $X_A$ and $X_p$ is greater than a threshold, this indicates an invalid reading. However, as noted above, only the one of the sensors having the highest error above the threshold will be selected as replacement value by the multiplexer 86 for the next cycle. This is due to the fact that the network 180 is trained on all of the input variables and each of the input variables will affect the predicted values for the remaining ones. Therefore, if the actual input values associated with predicted output values having an error greater than the threshold were replaced, this would not be as accurate as iteratively replacing one at a time.

Figure 11:
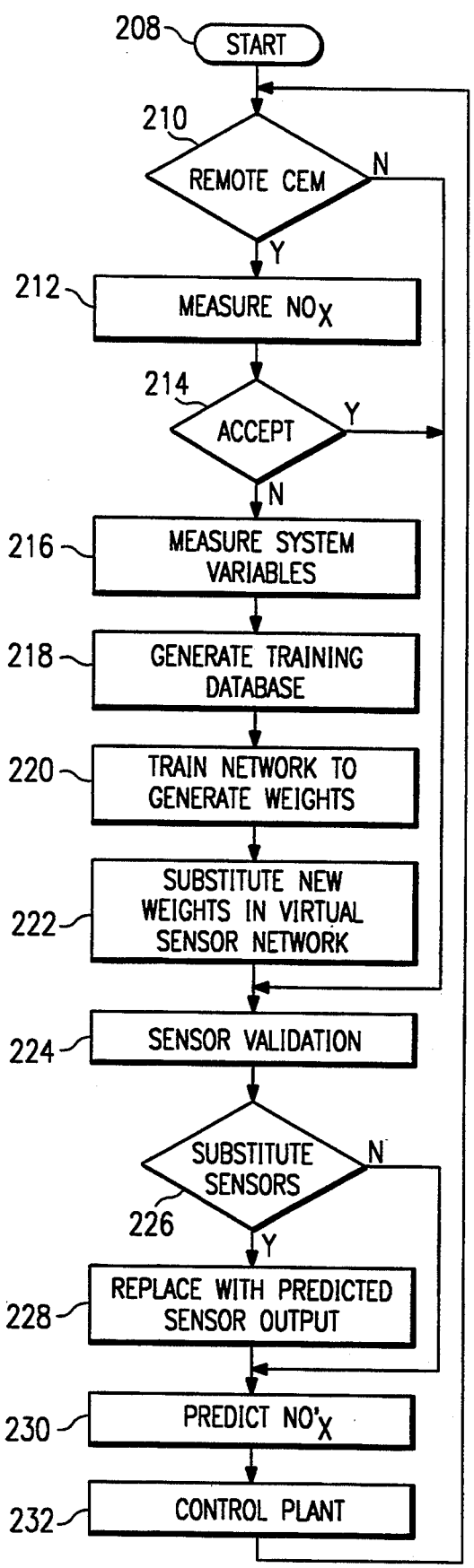
FIG. 11 illustrates a flowchart for operating the overall system.

Referring now to FIG. 11, there is illustrated a flowchart depicting the overall operation of the system. The flowchart is initiated at a start block 208 and then flows to a decision block 210. Decision block 210 determines whether the remote CEM has been installed. If so, the program then flows to a function block 212 to measure the NOx levels with the remote CEM. The program then flows to a decision block 214 to determine whether the measured NOx values, measured in function block 212, are acceptable. If not, this indicates that the virtual sensor network 18 is out of spec and that the system has either changed or the network no longer represents the system. The program will then flow along an "N" path to a function block 216 to measure the system variables and then to a function block 218 to generate a training database. A training database essentially utilizes the system variables that are measured along the same time base as the measured NOx levels. Typically, the remote CEM will be placed adjacent to the manufacturing facility and the pollutants measured for a predetermined amount of time, which can be measured in hours, days or weeks. At the same time, the plant facility itself is measuring the plant variables. These are also placed on a time base and stored. By merging the two data sets, a training database can be provided for training the virtual sensor network 18. This time merging operation is described in U.S. patent application Ser. No. 07/980,664, filed Nov. 24, 1992 and entitled "Method and Apparatus for Operating a Neural Network with Missing and/or Incomplete Data" (Atty. Dkt. No. PAVI-20,965).

Once the training database has been generated, the virtual sensor network 18 is trained, as indicated by a function block 220. This essentially generates weights, which can then be substituted for the neural network weights in the virtual sensor network 18. The program then flows to a function block 222 to substitute new weights in the virtual sensor network 18. Thereafter, the program flows to a main operating portion of the program, which is initiated at a function block 224 to validate the sensors.

If the pollutant parameters measured in the function block 212 were acceptable, the program would flow from the decision block 218 along a "Y" path to the input of function block 224 to bypass the training step. Additionally, if the remote CEM is not present, the program would flow along an "N" path from the decision block 210 to the input of the sensor validation block 224.

The sensor validation block 224 validates the sensors and, if one is found invalid, it substitutes a predicted value for that invalid sensor. The program would then flow to a function block 226 to determine if certain sensors needed to be replaced by predicted values. If so, the program would flow along a "Y" path to replace the invalid sensors with the predicted sensor value. The program would then flow to a function block 232 to predict the pollutant value and then to a function block 232 to control the plant. The program would then flow back to a decision block 210. If it were determined that sensors did not need to be replaced by their predicted values, the program would flow along an "N" path from the decision block 226 to the input of function block 230.

Figure 12:
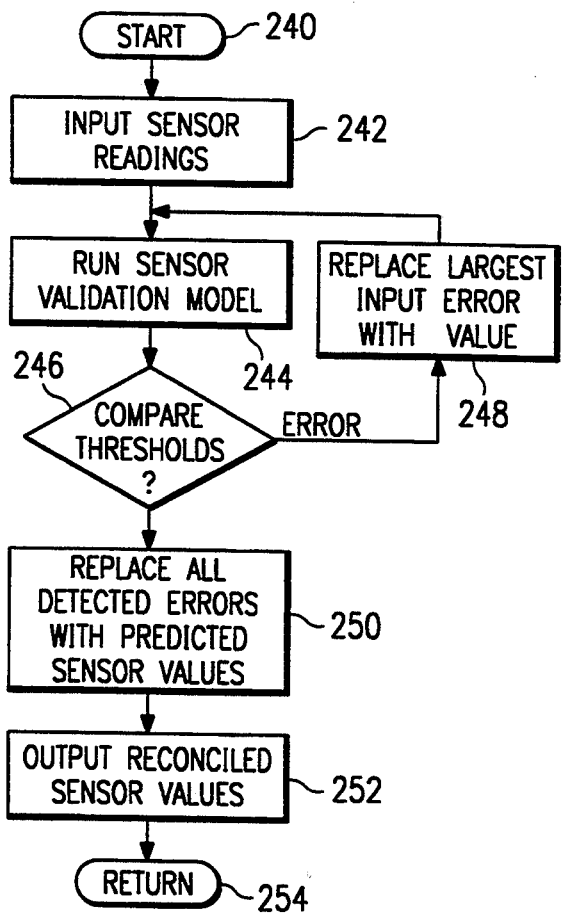
FIG. 12 illustrates a flowchart for the sensor validation operation.

Referring now to FIG. 12, there is illustrated a function block depicting the operation of the sensor validation. The program is initiated at a start block 240 and then flows to a function block 242 to input the various sensor readings. The program then flows to a function block 244 to run the sensor validation model and then to a decision block 246 to compare the predicted input values with the thresholds and generate an error signal when any of the predicted input values exceed the thresholds for that given variable, it being noted that there can be a threshold for each variable as to what constitutes an error for that sensor value. When an error exists, the program flows to a function block 248 to replace the largest input error with the mean value for that input. An alarm is generated at this point to warn of the failed sensor. The program will then flow back the input of a function block 244.

When the system has iteratively determined that there are no longer any predictive outputs that exceed these thresholds, the program will flow from a decision block 246 to a function block 250 to replace all detected errors with predicted sensor values and then to a function block 252 to output reconciled sensor values. The program will then flow to a return block 254.

Although the preferred embodiment has been described in detail, it should be understood that various changes, substitutions and alterations can be made therein without departing from the spirit and scope of the invention as defined by the appended claims.

What is claimed is:

1. A method for monitoring emissions in a manufacturing plant that are generated as a by-product of the operation of the plant, the manufacturing plant having controls operating in response to received control values to alter the operation of the plant and sensors to measure the operating parameters of the plant and output associated sensor values, comprising the steps of:

measuring on a periodic basis the level of pollutants emitted by the plant;

measuring the control values to the plant and the sensor values;

storing a representation of the plant in a virtual sensor predictive network having as an output a predicted pollutant level that corresponds to the actual pollutant level output by the manufacturing plant, the control values of the plant and the sensor values of the plant comprising inputs to the virtual sensor predictive network, the stored representation learned from the measured pollutant level, the control values and the sensor values, the virtual sensor predictive network operable to be trained upon the measured level of pollutants, the measured control values and the sensor values to generate the stored representation;

generating an error when the difference between the measured level of pollutants and the predicted pollutant level exceeds a predetermined threshold;

retraining the virtual sensor predictive network upon the generation of an error; and controlling the plant utilizing the predicted pollutant level in accordance with a predetermined control scheme to vary the control values.

2. The method of claim 1, wherein the step of periodically measuring the level of pollutants comprises periodically disposing an external emissions sensor in a predetermined location within the manufacturing plant to measure the level of pollutants emitted by the plant and, after the level of pollutants is measured, removing the external emissions sensor.

3. The method of claim 1, wherein the step of measuring the control values to the plant and the sensor values comprises measuring only select ones of the control values to the plant and select ones of the sensor values to comprise inputs to the virtual sensor predictive network such that only the ones of the control values and the ones of the sensor values that substantially affect the predicted pollutant level output of the virtual sensor predictive network are selected.

4. The method of claim 1, wherein the virtual sensor predictive network comprises a neural network, wherein the step of storing the representation of the plant comprises:

providing an input layer and inputting to the input layer the control values and the sensor values;

providing an output layer that is operable to output at least the predicted pollutant level; and providing at least one hidden layer and storing the representation of the plant in the hidden layer and mapping the input layer to the output layer through the stored representation in the at least one hidden layer.

5. The method of claim 4, and further comprising, storing the measured level of pollutants, the measured control values and the sensor values in a training database and training the neural network on the training database using the measured level of pollutants as a target output.

6. The method of claim 1, wherein the step of storing the representation of the plant in a virtual sensor predictive network comprises storing the representation of the plant in a non-linear virtual sensor predictive network.

7. The method of claim 1, wherein the step of controlling the plant utilizing a predicted pollutant level comprises controlling the pollutant level output by the plant utilizing a predicted pollutant level to maintain the predicted pollutant level within a predetermined range.

8. The method of claim 1, and further comprising:

determining if any of the sensor values are outside of acceptable limits that are defined for each of the associated sensors, in accordance with predetermined criteria; and substituting an associated known value for each of the sensor values determined to be outside of the acceptable limits for the associated sensor.

9. The method of claim 8, wherein the step of substituting comprises predicting from a past history of the sensor values associated with the sensor determined to have a sensor value outside of the associated acceptable limits, a predicted value, the predicted value comprising the known value for that sensor.

10. The method of claim 9, wherein the past history is a function of the sensor values for the other sensors.

11. The method of claim 8, wherein the step of determining comprises:

providing a sensor validation predictive network having as an input the actual sensor values of the plant, the sensor validation predictive network having associated therewith a stored representation of each of the actual sensor values as a function of the other of the actual sensor values to provide on the output thereof a predicted sensor value for each of the actual sensor values input thereto;

predicting with the predictive network the predicted sensor values; and comparing each of the differences of the input actual sensor values and the predicted sensor values with predetermined limits for those differences.

12. The method of claim 11, herein the step of substituting comprises replacing each of the actual sensor values that are input to the sensor validation predictive network with the predicted sensor values of the ones of the predicted sensor values determined to be outside of the predetermined limits.

13. A method for monitoring emissions in a manufacturing plant that is operable to generate pollutants, the manufacturing plant having controls operating in response to received control values to alter the operation of the plant and sensors to measure the operating parameters of the plant and output associated sensor values, comprising the steps of:

storing a representation of the plant in a virtual sensor predictive network having as an output a predicted pollutant level that corresponds to the actual pollutant level output by the manufacturing plant, the control values of the plant and the sensor values of the plant comprising inputs to the virtual sensor predictive network, the stored representation learned from the measured pollutant level, the control values and the sensor values;

determining if the sensor values for any of the sensors are outside of acceptable limits in accordance with predetermined criteria, which predetermined criteria is defined for each of the sensors; and substituting a known value for the sensor values of the ones of the sensors having sensor values determined to be outside of the acceptable limits by predicting from a past history of the sensor value to be substituted, a predicted sensor value for that sensor value, the predicted sensor value comprising the known value.

14. The method of claim 13, wherein the past history is a function of the sensor values associated with the other sensors.

15. The method of claim 13, wherein the step of determining comprises:
   providing a sensor validation predictive network having as an input the actual sensor values output by the plant, the sensor validation predictive network having associated therewith a stored representation of each of the actual sensor values for each of the sensors as a function of the actual sensor values of the other of the sensors to provide on the output thereof the predicted sensor value for each of the actual sensor values input thereto;
   predicting with the sensor validation predictive network the predicted sensor values; and
   comparing the difference of the input sensor values with the predicted sensor values with predetermined limits for that difference.

16. The method of claim 15, wherein the step of substituting comprises replacing each of the actual sensor values that are input to the sensor validation predictive network with the predicted sensor values of the ones of the predicted sensor values determined to be outside of the predetermined limits.

17. A system for monitoring emissions in a manufacturing plant that are generated as a by-product of the operation of the plant, the manufacturing plant having controls operating in response to received control values to alter the operation of the plant and sensors to measure the operating parameters of the plant and output associated sensor values, comprising:
   a pollutant sensor for measuring on a periodic basis the level of pollutants emitted by the plant;
   a plant information system for measuring the control values to the plant and the sensor values of the plant;
   a virtual sensor predictive network for storing a representation of the plant and having as an output a predicted pollutant level that corresponds to the actual pollutant level output by the manufacturing plant, the control values of the plant and the sensor values of the plant from said plant information system comprising inputs to said virtual sensor predictive network, the stored representation learned from the measured pollutant level, the control values and the sensor values, said virtual sensor predictive network operable to be trained upon the measured level of pollutants, the measured control values and the sensor values to generate the stored representation;
   said pollutant sensor operable to compare the measured level of pollutants with the predicted pollutant level output by said virtual sensor predictive network and generate an error when the difference between the measured level of pollutants and the predicted pollutant level exceeds a predetermined threshold;
   a training system for retraining said virtual sensor network upon the generation of an error; and
   a controller for controlling the plant utilizing the predicted pollutant level output by said virtual sensor predictive network in accordance with a predetermined control scheme to vary the control values.

18. The system of claim 17, wherein said plant information system is operable to measure only select ones of the control values to the plant and select ones of the sensor values to comprise inputs to said virtual sensor predictive network such that only the ones of the control values and the ones of the sensor values that substantially affect the predicted pollutant level output of said virtual sensor predictive network are selected.

19. The system of claim 17, wherein said virtual sensor predictive network comprises a neural network, said neural network comprising:
   an input layer for receiving as inputs the control values and the sensor values;
   an output layer that is operable to output at least the predicted pollutant level; and
   at least one hidden layer for storing the representation of the plant therein and mapping said input layer to said output layer through the stored representation in said at least one hidden layer.

20. The system of claim 19, and further comprising, a training database for storing the measured level of pollutants, the measured control values and the sensor values and a training system for training said neural network on said training database using the measured level of pollutants as a target output.

21. The system of claim 17, wherein said virtual sensor predictive network comprises a non-linear virtual sensor predictive network.

22. The system of claim 17, wherein said controller is operable to control the pollutant level output by the plant utilizing said predicted pollutant level to maintain the predicted pollutant level within a predetermined range.

23. The system of claim 17, and further comprising:
   a sensor validation system for determining as invalid the sensor values if the sensor values are outside of acceptable limits that are defined for each of the associated sensors, in accordance with predetermined criteria; and
   a substitute sensor for substituting a known value for each of the sensor values determined to be outside of the acceptable limits, each sensor having a known value associated therewith.

24. The system of claim 23, wherein said substitute sensor comprises a predictive network for generating a predicted sensor value for the invalid one of the sensor values from a past history of the sensor values to be substituted, said predicted sensor value comprising said known value.

25. The system of claim 24, wherein said past history is a function of the sensor values for the other sensors.

26. The system of claim 23, wherein said sensor validation system comprises:
   a sensor validation predictive network having as an input select ones of the actual sensor values of the plant, said sensor validation predictive network having associated therewith a stored representation of each of the select actual sensor values as a function of the other of the input actual sensor values to provide on the output thereof a predicted value for each of the actual sensor input thereto; and
   a comparator for comparing each of the differences of the input actual sensor values and the predicted sensor values with predetermined limits for those differences.

27. The system of claim 26, wherein said substitute sensor comprises a switching device for replacing each of the select actual sensor values that are input to said sensor validation predictive network with the predicted values of the ones of the predicted values determined to be outside of the predetermined limits.

28. A system for monitoring emissions in a manufacturing plant that is operable to generate pollutants, the manufacturing plant having controls operating in response to received control values to alter the operation of the plant and sensors to measure the operating parameters of the plant and output associated sensor values, comprising:
a virtual sensor predictive network for storing a representation of the plant and having as an output a predicted pollutant level that corresponds to the actual pollutant level output by the manufacturing plant, the control values to the plant and the sensor values of the plant comprising inputs to said virtual sensor predictive network, the stored representation learned from the measured pollutant level, the control values and the sensor values;
a sensor validation system for determining if select ones of the sensor values associated with select ones of the sensors are outside of acceptable limits in accordance with predetermined criteria; and
a substitute sensor for substituting a known value for the select sensor values when it is determined that they are outside of the acceptable limits, said substitute sensor comprising a predictive network for generating a predicted value for the one of the select sensor values determined to be outside of the acceptable limits, said predictive network generating said predicted value from a past history of the select sensor value to be substituted, said predicted value comprising said known value.

29. The system of claim 28, wherein the past history is a function of the select sensor values from other of the select sensors.

30. The system of claim 28, wherein said sensor validation system comprises:
a sensor validation predictive network having as an input select ones of the actual sensor values of the plant, said sensor validation predictive network having associated therewith a stored representation of each of the select actual sensor values as a function of the other of the input actual sensor values to provide on the output thereof a predicted value for each of the actual sensor values input thereto; and
a comparator for comparing each of the differences of the input actual sensor values and the predicted sensor values with predetermined limits for sensor value inputs.

31. The system of claim 30, wherein said substitute sensor comprises a switching device for replacing each of the select actual sensor values that are input to said sensor validation predictive network with the predicted values of the ones of the predicted values determined to be outside of the predetermined limits.

32. A method for monitoring emissions in a manufacturing plant that are generated as a by-product of the operation of the plant, the manufacturing plant having controls operating in response to received control values to alter the operation of the plant and sensors to measure the operating parameters of the plant and output associated sensor values, comprising the steps of:
measuring the level of pollutants emitted by the plant as a function of time;
measuring the control values to the plant and the sensor values as a function of time, the measured level of pollutants and the measured control values and sensor values providing a training dataset;
storing a representation of the plant in a virtual sensor predictive network having as an output a predicted pollutant level that corresponds to the actual pollutant level output by the manufacturing plant, the control values of the plant and the sensor values of the plant comprising inputs to the virtual sensor predictive network, the stored representation learned by training the virtual sensor predictive network on the training dataset; and
controlling the plant utilizing the predicted pollutant level in accordance with a predetermined control scheme to vary the control values.

33. The method of claim 32, wherein the step of measuring the level of the pollutants emitted by the plant comprises measuring the level of pollutants emitted by the plant at least one time in order to learn and store the representation of the plant in the virtual sensor predictive network.

34. The method of claim 33, wherein the step of measuring the level of pollutants at least one time comprises:
measuring the level of pollutants on a periodic basis and comparing it with the predicted pollutant level and generating an error when the difference between the measured level of pollutants and the predicted pollutant level exceeds a predetermined threshold; and
retraining the network upon the generation of an error.

35. The method of claim 34, wherein the step of periodically measuring the level of pollutants comprises periodically disposing an external emissions sensor in a predetermined location within the manufacturing plant to measure the level of pollutants emitted by the plant and, after the level of pollutants is measured, removing the external emissions sensor.

36. The method of claim 32, wherein the step of measuring the control values to the plant and the sensor values comprises measuring only select ones of the control values to the plant and select ones of the sensor values to comprise inputs to the virtual sensor predictive network such that only the ones of the control values and the ones of the sensor values that substantially affect the predicted pollutant level output of the virtual sensor predictive network are selected.

37. The method of claim 32, wherein the virtual sensor predictive network comprises a neural network, wherein the step of storing the representation of the plant comprises:
providing an input layer and inputting to the input layer the control values and the sensor values;
providing an output layer that is operable to output at least the predicted pollutant level; and
providing at least one hidden layer and storing the representation of the plant in the hidden layer and mapping the input layer to the output layer through the stored representation in the at least one hidden layer.

38. The method of claim 32, wherein the step of storing the representation of the plant in the virtual sensor predictive network comprises storing the representation of the plant in a non-linear virtual sensor predictive network.

39. The method of claim 32, wherein the step of controlling the plant utilizing a predicted pollutant level comprises controlling the pollutant level output by the plant utilizing a predicted pollutant level to maintain the predicted pollutant level within a predetermined range.

40. The method of claim 32, and further comprising:
determining if any of the sensor values or any of the control values are outside of acceptable limits that are defined for each of the sensor values and control values in accordance with predetermined criteria; and
substituting an associated known value for the each of the sensor values or each of the control values determined to be outside of the acceptable limits.

41. The method of claim 40, wherein the step of substituting comprises predicting from a past history of the sensor value or control value to be substituted, a predicted value, the predicted value comprising the known value.

42. The method of claim 41, wherein the past history is a function of the other sensor values or control values.

43. The method of claim 40 wherein the step of determining comprises:
providing a sensor validation predictive network having as an input the actual sensor values of the plant, the sensor validation predictive network having associated therewith a stored representation of each of the actual sensor values as a function of the other of the actual sensor values to provide on the output thereof a predicted sensor value for each of the actual sensor values input thereto;
predicting with the sensor validation predictive network the predicted sensor values; and
comparing each of the differences of the input actual sensor values and the predicted sensor values with predetermined limits for those differences.

44. The method of claim 43, wherein the step of substituting comprises replacing each of the actual sensor values that are input to the sensor validation predictive network with the predicted sensor values of the ones of the predicted sensor values determined to be outside of the predetermined limits.

45. A method for monitoring emissions in a manufacturing plant that are generated as a by-product of the operation of the plant, the manufacturing plant having controls operating in response to received control values to alter the operation of the plant and sensors to measure the operating parameters of the plant and output associated sensor values, comprising the steps of:
measuring the level of pollutants emitted by the plant;
measuring the control values to the plant and the sensor values;
storing a representation of the plant in a virtual sensor neural network having as an output a predicted pollutant level that corresponds to the actual pollutant level output by the manufacturing plant by the steps of:
providing an input layer and inputting to the input layer the control values and the sensor values,
providing an output layer that is operable to output at least the predicted pollutant level, and
providing at least one hidden layer and storing the representation of the plant in the hidden layer and mapping the input layer to the output layer through the stored representation in the at least one hidden layer;
the control values of the plant and the sensor values of the plant comprising inputs to the input layer of the virtual sensor neural network, the stored representation learned from the measured pollutant level, the control values and the sensor values; and
controlling the plant utilizing the predicted pollutant level in accordance with a predetermined control scheme to vary the control values.

46. The method of claim 45, wherein the step of measuring the level of the pollutants emitted by the plant comprises measuring the level of pollutants emitted by the plant at least one time in order to learn and store the representation of the plant in the virtual sensor neural network.

47. The method of claim 46, wherein the step of measuring the level of pollutants at least one time comprises:
measuring the level of pollutants on a periodic basis and comparing it with the predicted pollutant level and generating an error when the predicted pollutant level exceeds a predetermined threshold;
the virtual sensor neural network operable to be trained upon the measured level of pollutants, the measured control values and the sensor values to generate the stored representation; and
retraining the virtual sensor neural network upon the generation of an error.

48. The method of claim 47, wherein the step of periodically measuring the level of pollutants comprises periodically disposing an external emissions sensor in a predetermined location within the manufacturing plant to measure the level of pollutants emitted by the plant and, after the level of pollutants is measured, removing the external emissions sensor.

49. The method of claim 45, wherein the step of measuring the level of pollutants emitted by the plant comprises measuring the level of pollutants emitted by the plant as a function of time and wherein the step of measuring the control values to the plant and the sensor values are performed as a function of time, the measured level of pollutants and the measured control values and sensor values providing a training dataset wherein the step of storing a representation of the plant in the virtual sensor neural network comprises training the virtual sensor neural network on the training dataset to generate the stored representation.

50. The method of claim 45, wherein the step of measuring the control values to the plant and the sensor values comprises measuring only select ones of the control values to the plants and select ones of the sensor values to comprise inputs to the virtual sensor neural network such that only the ones of the control values and the ones of the sensor values that substantially affect the predicted pollutant level output of the virtual sensor neural network are selected.

51. The method of claim 45, and further comprising, storing the measured level of pollutants, the measured control values and the sensor values in a training database and training the virtual sensor neural network on the training database using the measured level of pollutants as a target output.

52. The method of claim 45, wherein the step of controlling the plant utilizing a predicted pollutant level comprises controlling the pollutant level output by the plant utilizing a predicted pollutant level to maintain the predicted pollutant level within a predetermined range.

53. The method of claim 45, and further comprising:
determining if any of the sensor values or any of the control values are outside of acceptable limits that are defined for each of the sensor values and control values in accordance with predetermined criteria; and substituting an associated known value for the each of the sensor values or each of the control values determined to be outside of the acceptable limits.

54. The method of claim 53, wherein the step of substituting comprises predicting from a past history of the sensor value or control value to be substituted, a predicted value, the predicted value comprising the known value.

55. The method of claim 54, wherein the past history is a function of the other sensor values or control values.

56. The method of claim 53, wherein the step of determining comprises:
- providing a sensor validation predictive network having as an input the actual sensor values of the plant, the sensor validation predictive network having associated therewith a stored representation of each of the actual sensor values as a function of the other of the actual sensor values to provide on the output thereof a predicted sensor value for each of the actual sensor values input thereto;
- predicting with the sensor validation predictive network the predicted sensor values; and
- comparing each of the differences of the input actual sensor values and the predicted sensor values with predetermined limits for those differences.

57. The method of claim 56, wherein the step of substituting comprises replacing each of the actual sensor values that are input to the sensor validation predictive network with the predicted sensor values of the ones of the predicted sensor values determined to be outside of the predetermined limits.

58. A method for monitoring emissions in a manufacturing plant that is operable to generate pollutants, the manufacturing plant having controls operating in response to received control values to alter the operation of the plant and sensors to measure the operating parameters of the plant and output associated sensor values, comprising the steps of:
- storing a representation of the plant in a virtual sensor predictive network having as an output a predicted pollutant level that corresponds to the actual pollutant level output by the manufacturing plant, the control values of the plant and the sensor values of the plant comprising inputs to the virtual sensor predictive network, the stored representation learned from the measured pollutant level, the control values and the sensor values;
- providing a sensor validation predictive network having as an input the actual sensor values of the plant, the sensor validation predictive network having associated therewith a stored representation of each of the actual sensor values as a function of the other of the actual sensor values to provide on the output thereof a predicted sensor value for each of the actual sensor values input thereto;
- predicting with the sensor validation predictive network the predicted sensor values;
- determining the difference between the input sensor values for each of the sensors and the associated predicted sensor values;
- comparing the difference determined for each of the sensors with predetermined limits associated with each of the sensors for that difference: and
- substituting a known value for the sensor values of each of the sensors wherein the determined difference exceeds the predetermined limits.

59. The method of claim 58, wherein the step of substituting comprises predicting from a past history of the sensor value to be substituted, a predicted sensor value, the predicted sensor value comprising the known value.

60. The method of claim 59, wherein the past history is a function of the other sensor values.

61. The method of claim 58, wherein the step of substituting comprises replacing each of the actual sensor values that are input to the sensor validation predictive network with the predicted sensor values of the ones of the sensors having predicted sensor values determined to be outside of the predetermined limits.

62. A system for monitoring emissions in a manufacturing plant that are generated as a by-product of the operation of the plant, the manufacturing plant having controls operating in response to received control values to alter the operation of the plant and sensors to measure the operating parameters of the plant and output associated sensor values, comprising:
- a pollutant sensor for measuring the level of pollutants emitted by the plant;
- a plant information system for measuring only select ones of the control values to the plant and select ones of the sensor values of the plant;
- a virtual sensor predictive network for storing a representation of the plant and having as an output a predicted pollutant level that corresponds to the actual pollutant level output by the manufacturing plant, the select ones of the control values to the plant and the select ones of the sensor values of the plant from said plant information system comprising inputs to said virtual sensor predictive network, wherein only the ones of the control values to the plant and the ones of the sensor values from the plant that substantially affect the predicted pollutant level output of said virtual sensor predictive network are selected by said plant information system, the stored representation learned from the measured pollutant level, the control values and the sensor values; and
- a controller for controlling the plant utilizing the predicted pollutant level output by said virtual sensor predictive network in accordance with a predetermined control scheme to vary the control values.

63. The system of claim 62, wherein said pollutant sensor is operable to measure the level of pollutants emitted by the plant at least one time in order to learn and store the representation of the plant in the said virtual sensor predictive network.

64. The system of claim 63, wherein:
- said pollutant sensor is operable to measure the level of pollutants on a periodic basis and compare the measured level of pollutants with the predicted pollutant level output by said virtual sensor predictive network and generate an error when the difference between the predicted pollutant level and the measured level of pollutants exceeds a predetermined threshold;
- said virtual sensor predictive network operable to be trained upon the measured level of pollutants, the control values and the sensor values to generate the stored representation; and further comprising:
- a training system for retraining said virtual sensor predictive network upon the generation of an error.

65. The system of claim 62, wherein said virtual sensor predictive network comprises a neural network, said neural network comprising:
- an input layer for receiving as inputs the control values and the sensor values;
- an output layer that is operable to output at least the predicted pollutant level; and
- at least one hidden layer for storing the representation of the plant therein and mapping said input layer to said output layer through the stored representation in said at least one hidden layer.

66. The system of claim 65, and further comprising, a training database for storing the measured level of pollutants, the control values and the sensor values and a training system for training said neural network on said training database using the measured level of pollutants as a target output.

67. The system of claim 62, wherein said virtual sensor predictive network comprises a non-linear virtual sensor predictive network.

68. The system of claim 62, wherein said controller is operable to control the pollutant level output by the plant utilizing a predicted pollutant level to maintain the predicted pollutant level within a predetermined range.

69. The system of claim 62, and further comprising:
- a sensor validation system for determining as invalid the sensor values if the sensor values are outside of acceptable limits that are defined for each of the associated sensors, in accordance with predetermined criteria; and
- a substitute sensor for substituting a known value for each of the sensor values determined to be outside of the acceptable limits, each sensor having a known value associated therewith.

70. The system of claim 69, wherein said substitute sensor comprises a predictive network for generating a predicted sensor value for the invalid one of the sensor values from a past history of the sensor values to be substituted, said predicted sensor value comprising said known value.

71. The system of claim 70, wherein said past history is a function of the sensor values associated with the other sensors.

72. The system of claim 69, wherein said sensor validation system comprises:
- a sensor validation predictive network having as an input select ones of the actual sensor values of the plant, said sensor validation predictive network having associated therewith a stored representation of each of the select actual sensor values as a function of the other of the input actual sensor values to provide on the output thereof a predicted value for each of the actual sensor values input thereto; and
- a comparator for comparing each of the differences of the input actual sensor values and the predicted sensor values with predetermined limits for those differences.

73. The system of claim 69, wherein said substitute sensor comprises a switching device for replacing each of the select actual sensor that are input to said sensor validation predictive network with the predicted values of the ones of the predicted values determined to be outside of the predetermined limits.

74. A system for monitoring emissions in a manufacturing plant that are generated as a by-product of the operation of the plant, the manufacturing plant having controls responsive to received control values to alter the operation of the plant and sensors to measure the operating parameters of the plant and output associated sensor values, comprising:
- a pollutant sensor for measuring the level of pollutants emitted by the plant;
- a plant information system for measuring the control values to the plant and the sensor values of the plant;
- a virtual sensor neural network for storing a representation of the plant and having:
  - an input layer for receiving as inputs the control values and the sensor values,
  - an output layer that is operable to output at least a predicted pollutant level that corresponds to the actual pollutant level output by the manufacturing plant, the stored representation learned from the measured pollutant level, the control values and the sensor values, and
  - at least one hidden layer for storing the representation of the plant therein and mapping said input layer to said output layer through the stored representation in said at least one hidden layer; and
- a controller for controlling the plant utilizing the predicted pollutant level output by said virtual sensor neural network in accordance with a predetermined control scheme to vary the control values.

75. The system of claim 74, wherein said pollutant sensor is operable to measure the level of pollutants emitted by the plant at least one time in order to learn and store the representation of the plant in the said virtual sensor neural network.

76. The system of claim 75, wherein:
- said pollutant sensor is operable to measure the level of pollutants on a periodic basis and compare the measured level of pollutants with the predicted pollutant level output by said virtual sensor neural network and generate an error when the difference between the predicted pollutant level and the measured level of pollutants exceeds a predetermined threshold;
- said virtual sensor neural network operable to be trained upon the measured level of pollutants, the control values and the sensor values to generate the stored representation; and further comprising:
- a training system for retraining the virtual sensor neural network upon the generation of an error.

77. The system of claim 74, wherein said plant information system is operable to measure only select ones of the control values to the plant and select ones of the sensor values to comprise inputs to said virtual sensor neural network such that only the ones of the control values and the ones of the sensor values that substantially affect the predicted pollutant level output of said virtual sensor neural network are selected.

78. The system of claim 74, and further comprising, a training database for storing the measured level of pollutants, the control values and the sensor values and a training system for training said virtual sensor neural network on said training database using the measured level of pollutants as a target output.

79. The system of claim 74, wherein said controller is operable to control the pollutant level output by the plant utilizing the predicted pollutant level to maintain the predicted pollutant level within a predetermined range.

80. The system of claim 74, and further comprising:

a sensor validation system for determining as invalid the sensor values if the sensor values are outside of acceptable limits that are defined for each of the associated sensors, in accordance with predetermined criteria; and a substitute sensor for substituting a known value for each of the sensor values determined to be outside of the acceptable limits, each sensor having a known value associated therewith.

81. The system of claim 80, wherein said substitute sensor comprises a predictive network for generating a predicted sensor value for the invalid one of the sensor values from a past history of the sensor value to be substituted, said predicted sensor value comprising said known value.

82. The system of claim 81, wherein said past history is a function of the sensor values associated with the other sensors.

83. The system of claim 80, wherein said sensor validation system comprises:

a sensor validation predictive network having as an input select ones of the actual sensor values of the plant, said sensor validation predictive network having associated therewith a stored representation of each of the select actual sensor values as a function of the other of the input actual sensor values to provide on the output thereof a predicted value for each of the actual sensor values input thereto; and a comparator for comparing each of the differences of the input actual sensor values and the predicted sensor values with predetermined limits for those differences.

84. The system of claim 83, wherein said substitute sensor comprises a switching device for replacing each of the select actual sensor values that are input to said sensor validation predictive network with the predicted values of the ones of the predicted values determined to be outside of the predetermined limits.

85. A system for monitoring emissions in a manufacturing plant that is operable to generate pollutants, the manufacturing plant having controls responsive to control values to alter the operation of the plant and sensors outputting sensor values as a measure the operating parameters of the plant, comprising:

a virtual sensor predictive network for storing a representation of the plant and having as an output a predicted pollutant level that corresponds to the actual pollutant level output by the manufacturing plant, the control values of the plant and the sensor values of the plant comprising inputs to said virtual sensor predictive network, the stored representation learned from the measured pollutant level, the control values and the sensor values;

a sensor validation predictive network having as an input select ones of the actual sensor values of the plant and actual control values of the plant, said sensor validation predictive network having associated therewith a stored representation of each of the select actual sensor values and actual control values as a function of the other of the input actual sensor and control values to provide on the output thereof a predicted value for each of the actual sensor and control values input thereto; and a comparator for comparing each of the differences of the input actual sensor values and the predicted sensor values with predetermined limits for those differences to determine if select ones of the sensor and control values are outside of those predetermined limits; and a substitute sensor for substituting a known value for the select sensor or control values when it is determined that they are outside of the predetermined limits.

86. The system of claim 85, wherein said substitute sensor comprises a switching device for replacing each of the select actual sensor values that are input to said sensor validation predictive network with the predicted values of the ones of the predicted values determined to be outside of the predetermined limits.

* * * * *

UNITED STATES PATENT AND TRADEMARK OFFICE
CERTIFICATE OF CORRECTION

PATENT NO. : 5,386,373                  Page 1 of 3

DATED : January 31, 1995

INVENTOR(S) : James D. Keeler, et al.

It is certified that error appears in the above-indentified patent and that said Letters Patent is hereby corrected as shown below:

On the title page, the following references were cited and should be be added:

5,003,950
    5,025,499
    5,077,970
    5,088,314
    5,093,792
    5,113,483
    5,119,287
    5,119,468
    5,150,682
    5,163,412
    5,175,678
    5,177,464
    5,213,080
    5,220,905
    5,222,471
    5,228,335
    5,231,939
    5,251,285
    5,270,009
    5,271,674

UNITED STATES PATENT AND TRADEMARK OFFICE
CERTIFICATE OF CORRECTION

PATENT NO. : 5,386,373

DATED : January 31, 1995

INVENTOR(S) : James D. Keeler, et al.

It is certified that error appears in the above-indentified patent and that said Letters Patent is hereby corrected as shown below:

Column 6, line 55, equation (4), replace:

$$\vec{E} = \sum_{t=1}^{N} (\vec{y}(t) - \vec{o}(t))^2 \tag{4}$$

with $$\vec{E} = \sum_{t=1}^{M} (\vec{y}(t) - \vec{o}(t))^2 \tag{4}$$

UNITED STATES PATENT AND TRADEMARK OFFICE
CERTIFICATE OF CORRECTION

PATENT NO. : 5,386,373

DATED : January 31, 1995

INVENTOR(S) : James D. Keeler, et al.

It is certified that error appears in the above-indentified patent and that said Letters Patent is hereby corrected as shown below:

Column 23, claim 73, line 58, replace "69" with —72—.

Signed and Sealed this

Twenty-fifth Day of April, 1995

*Attest:*

BRUCE LEHMAN

*Attesting Officer*       *Commissioner of Patents and Trademarks*